United States Patent [19]
Szonntagh

[11] 4,415,278
[45] Nov. 15, 1983

[54] METHOD FOR OPERATING A GAS ANALYZING SYSTEM AND APPARATUS UTILIZING THE SAME

[75] Inventor: Eugene L. Szonntagh, Flourtown, Pa.

[73] Assignee: Honeywell Inc., Minneapolis, Minn.

[21] Appl. No.: 346,814

[22] Filed: Feb. 8, 1982

[51] Int. Cl.³ .......................................... G01N 25/22
[52] U.S. Cl. ................................................... 374/37
[58] Field of Search ................ 55/269; 62/93; 374/36, 374/37

[56] References Cited

U.S. PATENT DOCUMENTS

| | | | |
|---|---|---|---|
| 2,689,478 | 9/1954 | Barnard et al. | 374/37 |
| 3,777,562 | 12/1973 | Clingman, Jr. | 374/37 |
| 3,963,466 | 6/1976 | Hynes | 55/269 |
| 4,359,284 | 11/1982 | Kude et al. | 374/37 |
| 4,380,400 | 4/1983 | Searle | 374/37 |

Primary Examiner—Herbert Goldstein
Attorney, Agent, or Firm—Trevor B. Joike; Mitchell J. Halista

[57] ABSTRACT

A method and apparatus for a gas analyzing system uses a rotary valve for mixing fuel gas to be analyzed for calorific content and air. The speed of the rotary valve which determines the air-fuel ratio is controlled by a controller sensing combustion products resulting from a combustion of the fuel gas and air mixture. The control of the air-fuel ratio is arranged to produce a substantially stoichiometric combustion at which condition the calorific content of the fuel gas is determined from the controller operation. The air supplied to the rotary valve is initially pumped through a dehumidifier for removing water vapor to minimize the error in the measurement of the calorific content of the fuel gas produced by the entrained water vapor. The dehumidifier includes a labyrinth in the air flow path which is cooled by a thermoelectric cooler below the dew point temperature of the air stream but above the freezing point of water to produce a condensation of the entrained water vapor on the cooled surface. The condensed water is allowed to drain from the dehumidifier by a drain within the cooled environment while the dehumidified air is subsequently applied through a pressure regulator to the rotary mixing valve.

7 Claims, 3 Drawing Figures

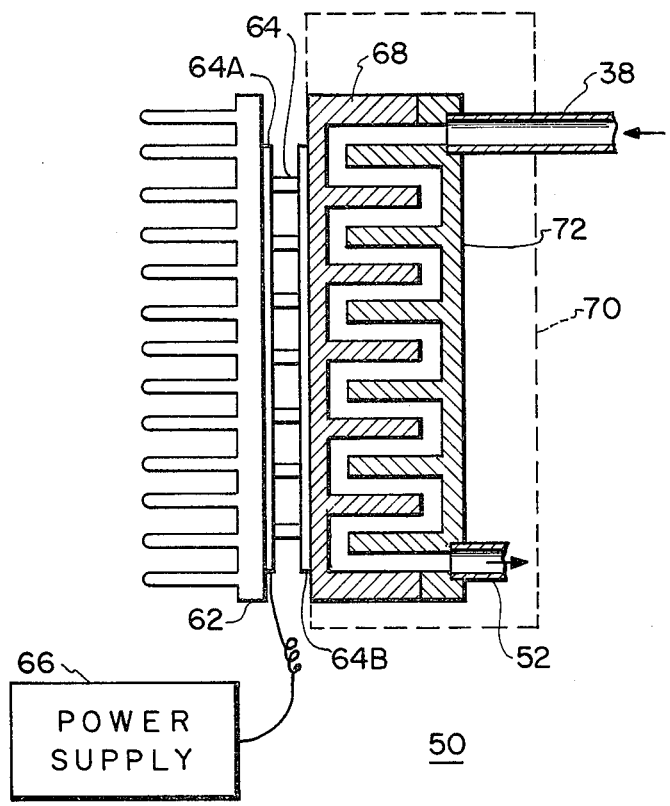
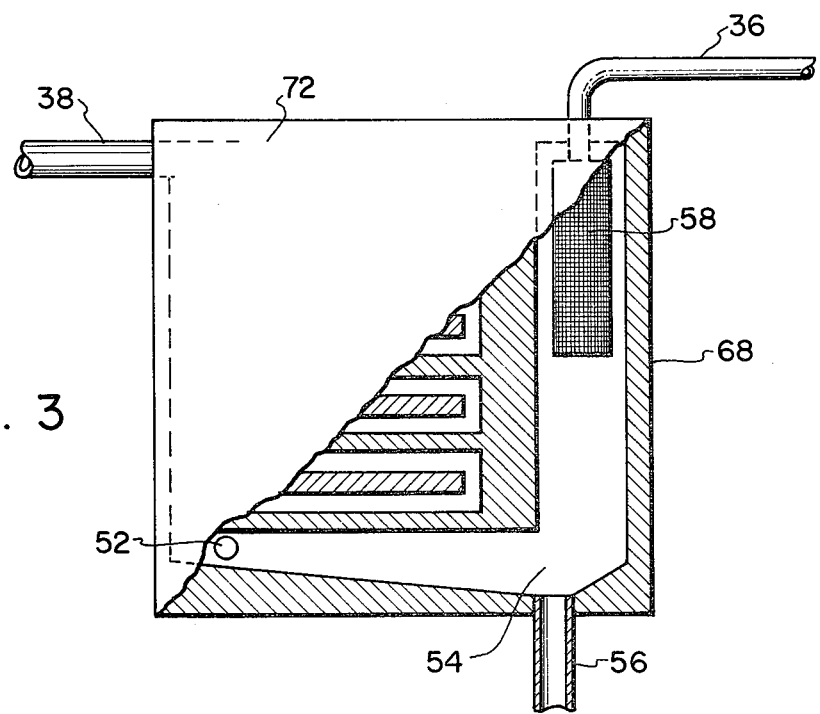

4,415,278

METHOD FOR OPERATING A GAS ANALYZING SYSTEM AND APPARATUS UTILIZING THE SAME

BACKGROUND OF THE INVENTION

1. Field of the Invention

The present invention relates to gas analyzers. More specifically, the present invention is directed to a method and apparatus for measuring the calorific content of a fuel gas.

SUMMARY OF THE INVENTION

An object of the present invention is to provide an improved gas analyzing apparatus for measuring the calorific content of a fuel gas.

In accomplishing this and other objects, there has been provided, in accordance with the present invention a gas analyzing apparatus for a fuel gas utilizing a selectively driven fuel gas and air mixing apparatus for controlling the air-fuel ratio supplied to a combustion device where the fuel gas and air mixture is subsequently burned. The control of the fuel gas and air ratio is controlled by a controller sensing the combustion products from the combustion of the fuel gas and air to achieve substantially stoichiometric combustion. The air supplied to the mixing device for producing the variable fuel gas and air ratio is initially dehumidified to remove entrained water vapor by a dehumidifier which cools the air stream by a thermoelectric cooler to a point below its dew point temperature but above the freezing point of water and allows the resulting condensed water to separate from the air stream prior to supplying the air to the fuel-air ratio producing apparatus.

BRIEF DESCRIPTION OF THE DRAWINGS

A better understanding of the present invention may be had when the following detailed description is read in connection with the accompanying drawings, in which:

FIG. 2 is a side view of the dehumidifier used in the system shown in FIG. 1 and FIG. 3 is a front view of the dehumidifier shown in FIGS. 1 and 2.

DETAILED DESCRIPTION OF THE DRAWINGS

Figure 1:
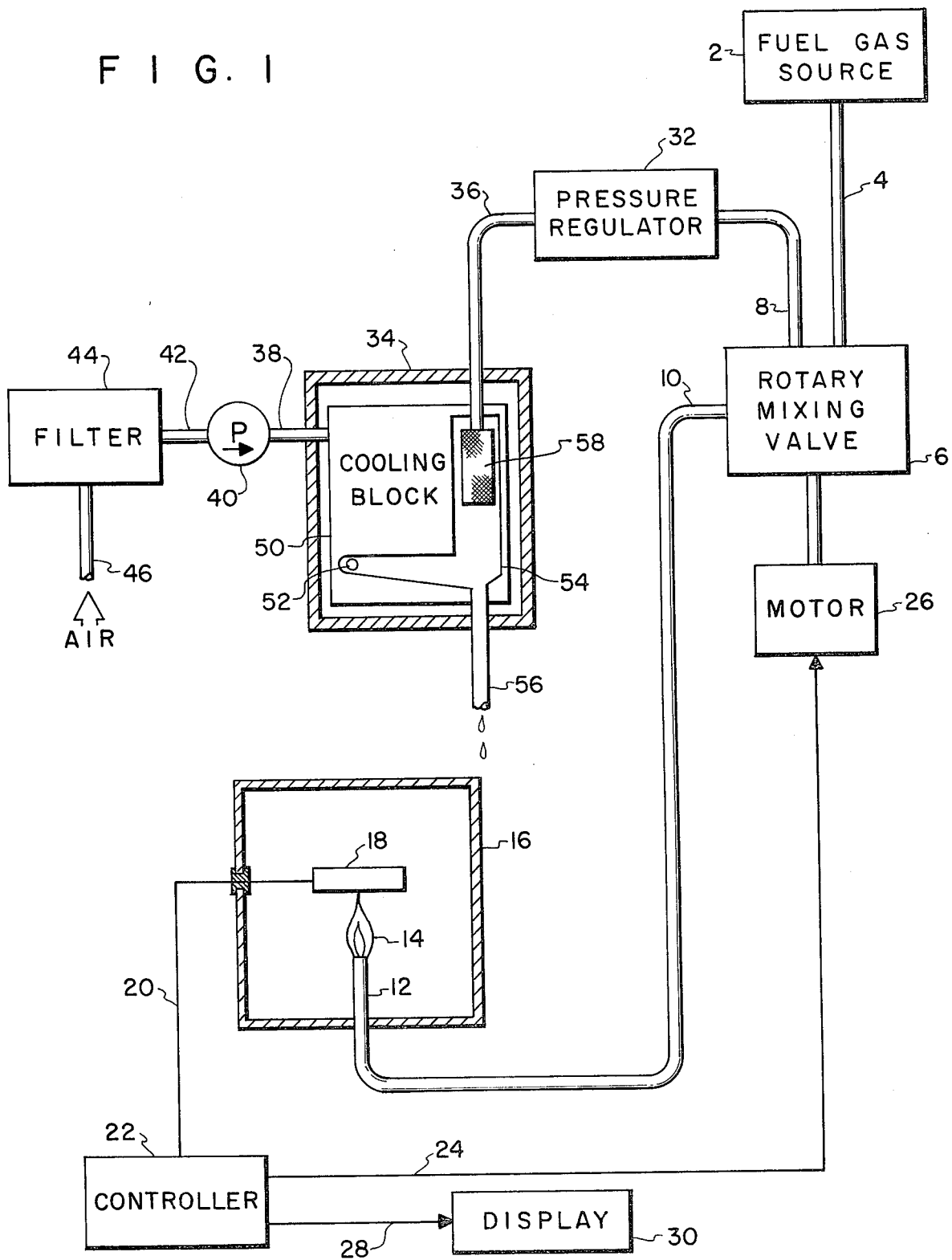
FIG. 1 is a pictorial illustration of an example of a gas analyzing apparatus embodying the present invention.

Referring to FIG. 1 in more detail, there is shown a gas analyzing apparatus for determining the calorific content of a fuel gas supplied from a fuel gas source 2. The fuel gas source 2 is connected by a pipeline 4 to a rotary mixing valve 6. A second input to the mixing valve 6 is connected to an air supply by a pipeline 8, as described more fully hereinafter. The mixing valve 6 is arranged to produce an output mixture of fuel gas and air having gas-air ratio which is dependent on the rotational speed of the valve 6, such devices being well-known in the art. While a rotary mixing valve has been shown for purposes of illustration, it should be noted that other types of devices for producing variable ratios of the fuel-air mixture could be substituted for the valve 6, e.g., solenoid operated valves in the air and fuel gas lines which are operated by variable duty cycle signals to produce valve open and closed durations.

The output from the mixing valve 6 is connected through an output pipeline 10 to a burner jet 12 for producing a combustion flame 14 within a combustion chamber 16. A sensor 18 for sensing the combustion products from the flame 14 is located within the chamber 16 adjacent to the flame 14. Specifically, the sensor 18 may be a zirconium oxide detector for detecting the excess oxygen in the combustion products whereby a substantially stoichiometric combustion of the fuel gas and air may be achieved wherein the oxygen in the combustion products is minimized. The output signal from the sensor 18 is representative of the detected oxygen level in the combustion products applied via a connecting wire 20 to a controller 22. The controller 22 is arranged to respond to the output signal from the sensor 18 to produce a first controller output signal on line 24 for controlling the speed of the motor 26 driving the rotary mixing valve 6, such devices being well-known in the art. Thus, the speed of the motor 26 is effective to control the air-fuel ratio whereby the substantially stoichiometric combustion within the combustion chamber 16 may be achieved. The controller 22 is also arranged to provide a second output signal on line 28 representative of the operation of the controller 22, e.g., the speed of the motor, for application to a display device 30 for providing a display of the calorific content of the fuel gas, e.g., the display device 30 may be digital display for displaying the calorific content in BTU'S.

The air providing the oxygen for the combustion process at the burner jet 12 is supplied to the mixing valve 6 through a pressure regulator 32. The input to the pressure regulator 32 is obtained from a dehumidifier 34 having an output pipeline 36 connected to the input of the pressure regulator 32. The input of the dehumidifier 34 is via a pipeline 38 connected to the output of a pump 40. The pump 40 has an inlet which is connected through a pipeline 42 to the outlet of a filter 44. The filter 44 has an inlet which is connected to an air inlet pipeline 46.

Within the dehumidifier assembly 34 is located a cooling block 50, having an inlet connected to the pipeline 38, for cooling the incoming air in the inlet pipeline 38 below its dew point temperature to produce condensation of the water vapor entrained in the air supplied from the air inlet pipeline 46. An outlet 52 located within the cooling block 50 provides an interconnection between an air cooling labyrinth, described more fully hereinafter, within the cooling block 50 and a drain chamber 54, also located within the cooling block 50, and connected to a drain conduit 56. The dehumidified air, subsequently, is directed to the output pipeline 36 through a filter element 58 within the drain chamber 54. By minimizing the water vapor in the air to be used for the combustion of the fuel gas, the determination of the calorific content of the fuel gas using the apparatus and method of the present invention is achieved with substantially greater accuracy by reducing the error produced by the water vapor entrained in the air.

In FIGS 2 and 3, there is shown a side and front view, respectively, of the cooling block 50 shown in the dehumidifier 34. The cooling block 50 includes a finned heat sink 62 having a thermo-electric cooling element 64 mounted thereon with a hot plate 64A in contact with the heat exchanger 62 and a cold plate 64B in contact with a dehumidifying heat exchanger element within the cooling block 50. The thermo-electric cooler 64 is powered by a power supply 66 to produce a heat transfer or cooling effect in a manner well-known in the art. The cold plate 64B is arranged to be in thermal contact with a dehumidifying element in the form of an air flow labyrinth formed between a grooved thermally conductive block 68 and a cover 70 for the thermally conductive block 68. The cover 70 is also grooved on an internal face and is attached to the block 68 by any suitable means (not shown). The internal grooved surfaces of the block 68 ahnd cover 74 form a labyrinth for the air flow therein between the inlet pipe 38 and the outlet 52. The backplate 68 and the cover 70 may advantageously be made of aluminum. A thermally insulating material 72 is arranged to enclose the cooling block 50 to maintain the temperature level therein produced by the thermo-electric cooler 64 to enhance the condensation of the water vapor from the air. The position of the drain chamber 54 and the drain conduit 56 inlet within the cooling block 50 prevents the condensed water vapor from being reevaporated into the air stream whereby a condensed water removal is maintained. The dehumidified air is allowed to flow through the filter 58 to the outlet pipeline 36 from the cooling block 50.

Accordingly, it may be seen that there has been provided, in accordance with the present invention an improved gas analyzing apparatus and method for measuring the calorific content of the fuel gas.

The embodiments of the invention in which an exclusive property or privilege is claimed are defined as follows:

1. A gas analyzing apparatus comprising
    a source of a fuel gas,
    a source of combustion air,
    ratio control means for producing a mixture of fuel gas and air in a selectively variable ratio, said means having a first and a second inlet and an outlet,
    means connecting said fuel gas source to said first inlet of said ratio control means,
    dehumidifying means connecting said source of air to said second inlet of said ratio control means to minimize water vapor entrained in the air from said source, said dehumidifying means including a cooling block having an internal labrynth air path, a cooling means including a thermo-electric cooler having a cold plate in thermal contact with said cooling block and a power supply for energizing said cooler and arranged to cool said cooling block below the dew point of air within said labrynth air path, but above the freezing point of water and a drain from said labrynth air path to remove condensed water from said cooling block,
    combustion means connected to said outlet from said ratio control means for producing a combustion of said mixture of fuel gas and air,
    sensor means for sensing combustion products from said combustion means to produce an output signal representative of the combustion state and
    controller means arranged to respond to an output from said sensor means for controlling said ratio control means to produce substantially stoichiometric combustion of said mixture of fuel gas and air.

2. A gas analyzing apparatus as set forth in claim 1 wherein said means for producing a mixture includes a rotary valve for mixing air and fuel gas and said controller means controls the speed of rotation of said rotary valve.

3. A gas analyzing apparatus as set forth in claim 1 wherein said controller means includes a display means for displaying the operation of said controller means as a representation of a characteristic of said fuel gas.

4. A gas analyzing apparatus as set forth in claim 3 wherein said characteristic is the calorific content of said fuel gas.

5. A gas analyzing apparatus as set forth in claim 1 wherein said dehumidifying means includes thermally insulated material enclosing the cooling block to maintain the temperature level therein produced by the thermo-electric cooler.

6. A gas analyzing apparatus as set forth in claim 1 wherein said labrynth air path includes a grooved thermally conductive block in contact with said thermo-electric cooler and a cover for said thermally conductive block having a grooved face facing the grooves in said block.

7. A gas analyzing apparatus as set forth in claim 1 wherein said source of combustion air includes a filter for filtering said combustion air and a pump for pumping said combustion air into said dehumidifying means.

* * * * *